(12) United States Patent
Risi

(10) Patent No.: US 7,966,077 B2
(45) Date of Patent: Jun. 21, 2011

(54) ELECTRODE ASSEMBLY FOR A STIMULATING MEDICAL DEVICE

(75) Inventor: Frank Risi, Newtown (AU)

(73) Assignee: Cochlear Limited, Macquarie University, NSW ( * ) Notice: Subject to any disclaimer, the term of this patent is extended or adjusted under 35 U.S.C. 154(b) by 237 days.

(21) Appl. No.: 11/529,269

(22) Filed: Sep. 29, 2006

(65) Prior Publication Data

US 2008/0082141 A1   Apr. 3, 2008

(51) Int. Cl.
A61N 1/00 (2006.01)
A61B 5/04 (2006.01)

(52) U.S. Cl. .......... 607/137; 607/55; 607/56; 607/57; 600/372; 600/393

(58) Field of Classification Search .......... 607/55, 607/57, 137; 600/372, 393
See application file for complete search history.

(56) References Cited

U.S. PATENT DOCUMENTS

| | | | |
|---|---|---|---|
| 4,284,856 A * | 8/1981 | Hochmair et al. | 607/9 |
| 4,357,497 A * | 11/1982 | Hochmair et al. | 607/5 |
| 4,832,051 A * | 5/1989 | Jarvik et al. | 607/116 |
| 5,069,210 A * | 12/1991 | Jeutter et al. | 607/57 |
| 5,330,520 A | 7/1994 | Maddison et al. | |
| 5,443,493 A * | 8/1995 | Byers et al. | 607/137 |
| 5,554,176 A | 9/1996 | Maddison et al. | |
| 5,571,148 A * | 11/1996 | Loeb et al. | 607/57 |
| 5,667,514 A * | 9/1997 | Heller | 606/108 |
| 5,843,093 A | 12/1998 | Howard, III | |
| 5,876,443 A * | 3/1999 | Hochmair et al. | 623/10 |
| 5,938,691 A * | 8/1999 | Schulman et al. | 607/57 |
| 6,125,302 A * | 9/2000 | Kuzma | 607/137 |
| 6,214,046 B1 * | 4/2001 | Kennedy | 623/10 |
| 6,216,040 B1 * | 4/2001 | Harrison | 607/57 |
| 6,263,225 B1 | 7/2001 | Howard, III | |
| 6,321,125 B1 * | 11/2001 | Kuzma | 607/137 |
| 6,374,143 B1 | 4/2002 | Berrang et al. | |
| 6,421,569 B1 | 7/2002 | Treaba et al. | |
| 6,604,283 B1 * | 8/2003 | Kuzma | 29/857 |
| 6,757,970 B1 * | 7/2004 | Kuzma et al. | 29/847 |
| 6,968,238 B1 * | 11/2005 | Kuzma | 607/137 |
| 7,063,708 B2 | 6/2006 | Gibson et al. | |

(Continued)

OTHER PUBLICATIONS

International Search Report for PCT/US2007/080109 dated Apr. 16, 2008.

(Continued)

*Primary Examiner* — Niketa I Patel
*Assistant Examiner* — Nicole F Lavert
(74) *Attorney, Agent, or Firm* — Kilpatrick Townsend & Stockton LLP

(57) ABSTRACT

An electrode assembly comprising a low-profile, low-volume elongate electrode carrier and a corresponding guide tube for introducing the carrier into the cochlea to place electrodes disposed at the distal end of the carrier at desired locations along the tonotopically-mapped cochlea. The electrode assembly facilitates intra- and extra-cochlea atraumatic implantation of the unobtrusive electrode carrier of the present invention thereby minimizing adverse impact to natural auditory functioning. For example, the electrode assembly may be utilized to implant the low-profile, low-volume elongate electrode carrier into the scala tympani without damaging the delicate structures of the cochlea and without interfering with the natural hydrodynamic nature of the cochlea such as the natural flow of perilymph in the cochlea canals. In one particular embodiment, the carrier is pre-curved to attain a perimodiolar position in the scala tympani to facilitate accurate delivery of electrical stimulation with a minimum stimulation current and power consumption.

72 Claims, 14 Drawing Sheets

U.S. PATENT DOCUMENTS

| | | | |
|---|---|---|---|
| 7,146,227 B2* | 12/2006 | Dadd et al. | 607/137 |
| 2003/0181967 A1* | 9/2003 | Dadd et al. | 607/122 |
| 2004/0172118 A1 | 9/2004 | Gibson | |
| 2004/0236390 A1* | 11/2004 | Dadd et al. | 607/55 |
| 2004/0243212 A1* | 12/2004 | Dadd et al. | 607/137 |
| 2005/0203557 A1* | 9/2005 | Lesinski | 606/180 |
| 2007/0106344 A1* | 5/2007 | Darley et al. | 607/55 |
| 2007/0129772 A1* | 6/2007 | Loeb | 607/57 |
| 2007/0255344 A1* | 11/2007 | Van Dijk | 607/57 |

OTHER PUBLICATIONS

Written Opinion for PCT/US2007/080109 dated Apr. 16, 2008.
International Preliminary Report on Patentability for PCT/US2007/080109 dated Dec. 20, 2008.

* cited by examiner

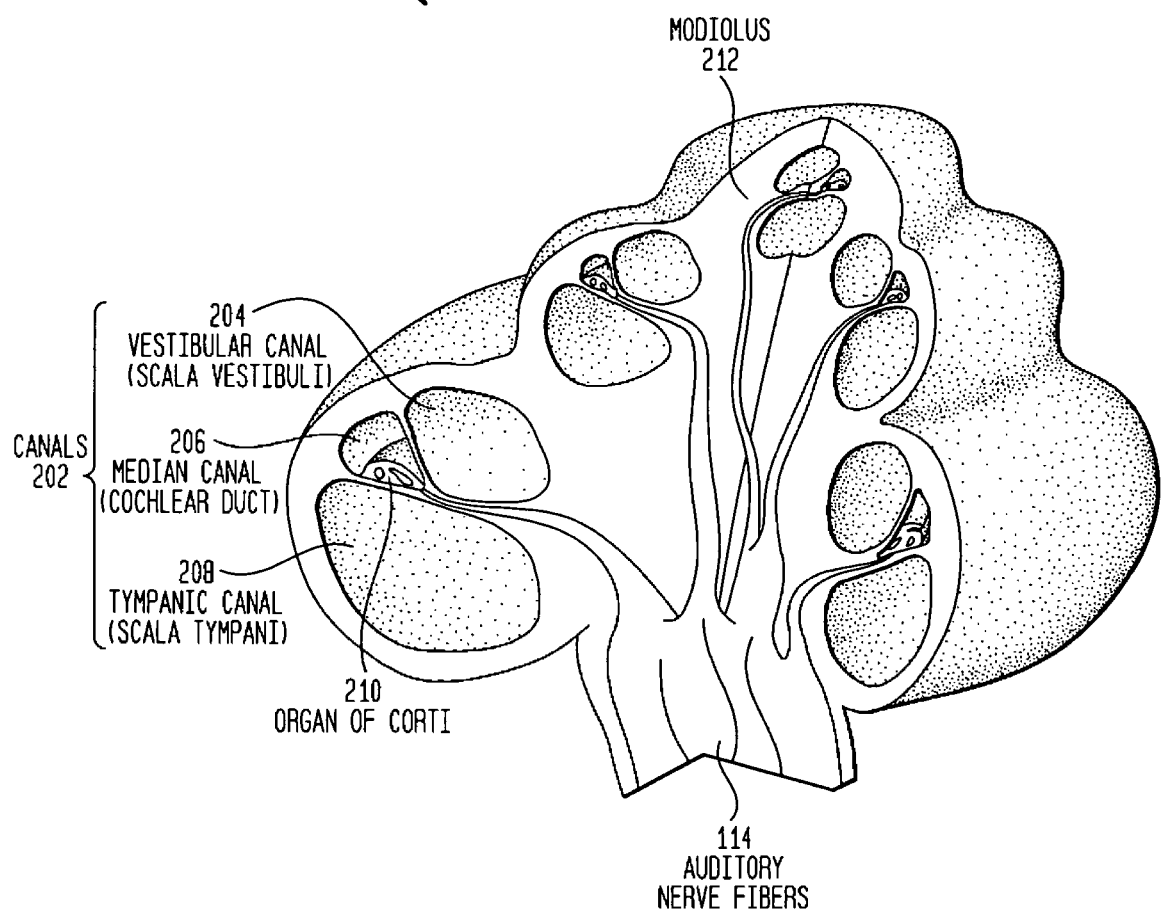

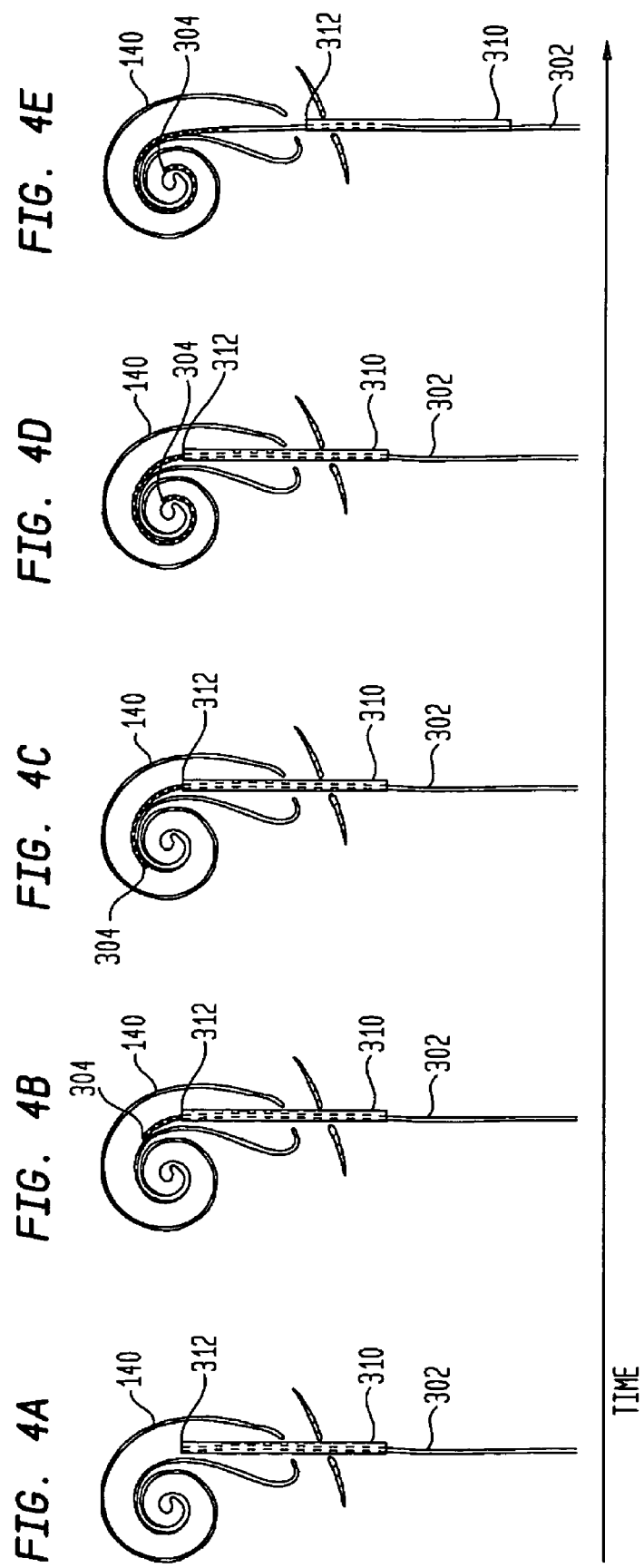

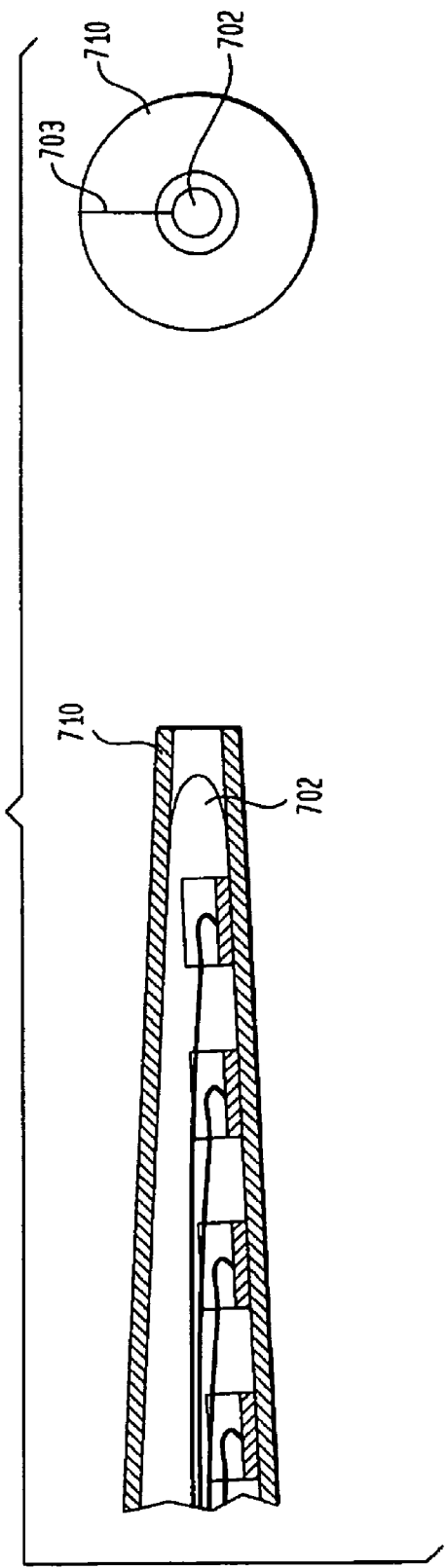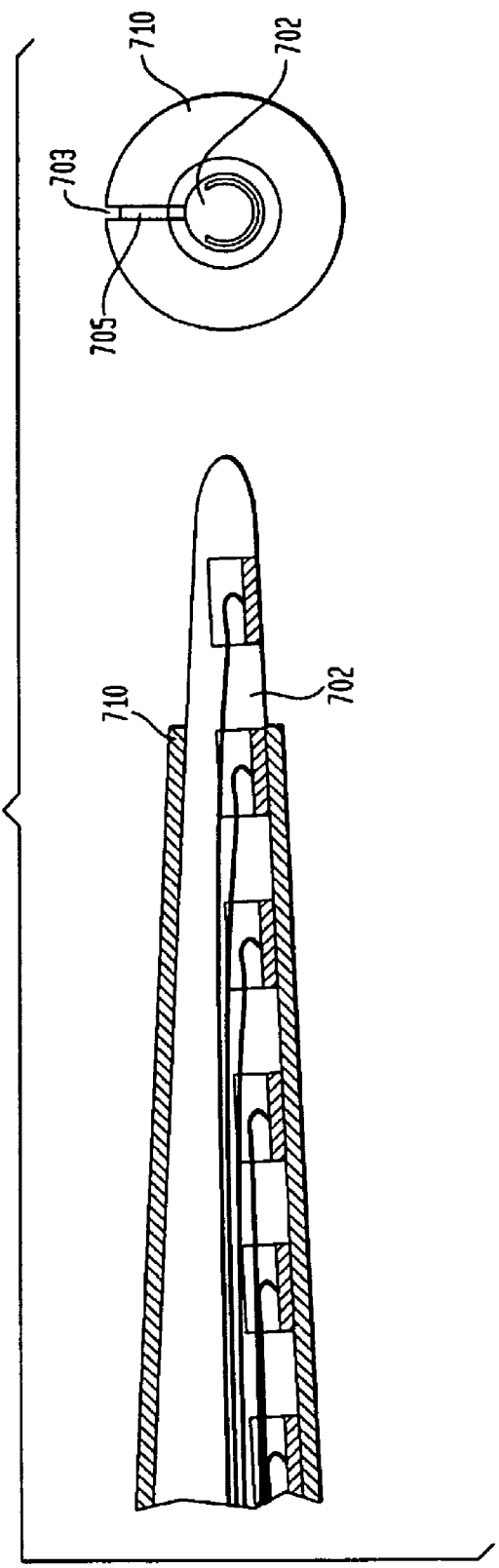

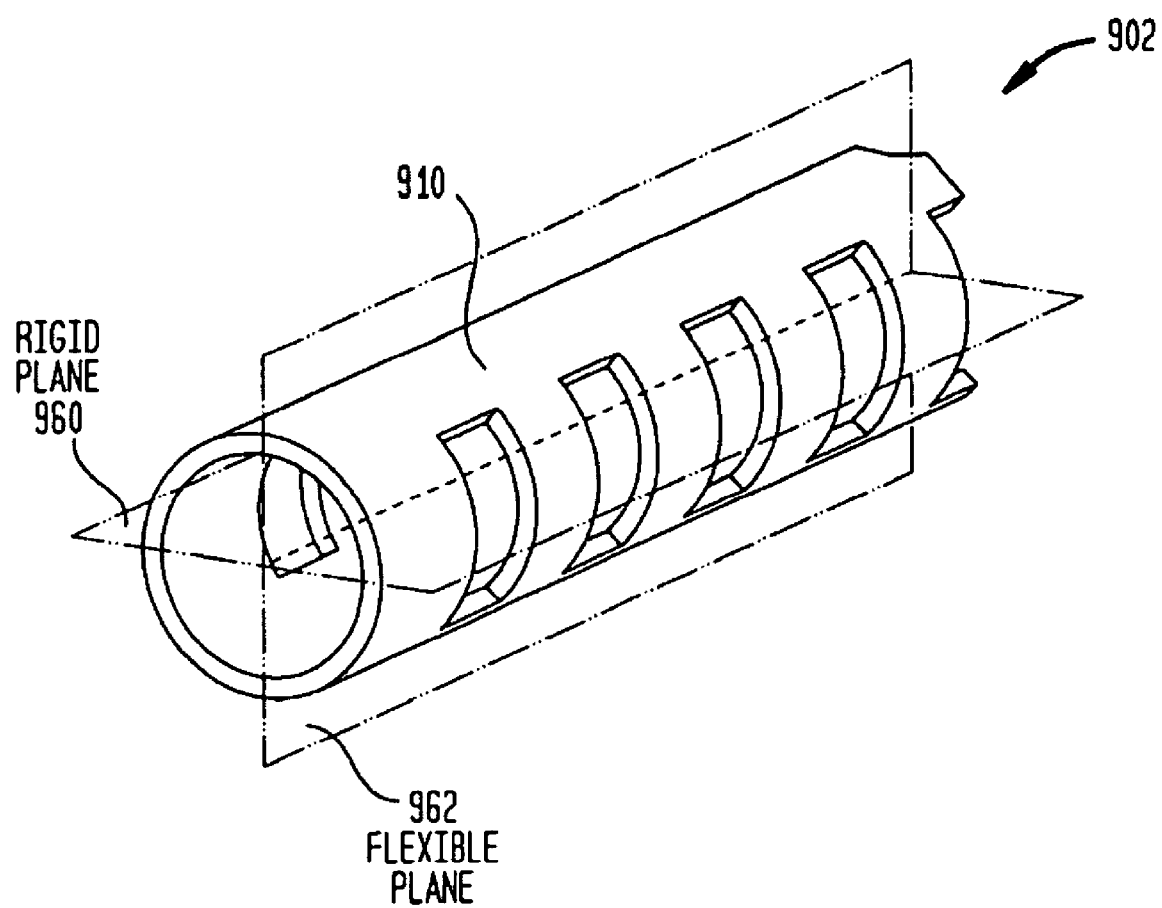

ELECTRODE ASSEMBLY FOR A STIMULATING MEDICAL DEVICE

BACKGROUND

1. Field of the Invention

The present invention relates generally to a stimulating medical devices and, more particularly, to an electrode assembly for a stimulating medical device.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to or absence of the mechanism for naturally generating nerve impulses from sound.

It is for this purpose that another type of auditory prosthesis, a COCHLEAR™ implant (also commonly referred to as COCHLEAR™ prosthesis, COCHLEAR™ devices, COCHLEAR™ implant devices, and the like, generally and collectively referred to herein as "cochlear implants") has been developed. Stimulating auditory prostheses such a cochlear implants bypass the hair cells in the cochlea, directly delivering electrical stimulation to the auditory nerve fibers via an implanted electrode assembly. This enables the brain to perceive a hearing sensation resembling the natural hearing sensation normally delivered to the auditory nerve.

Despite the enormous benefits offered by cochlear implants, one potential disadvantage is that the implanted electrode carrier member is located within the internal canals of the cochlea, generally the scala tympani. Breaching the scala tympani may adversely affect the hydrodynamic behavior of the cochlea and/or damage existing hair cells thereby preventing or at least reducing the likelihood that any residual hearing will be preserved. This may be problematic for those persons who would benefit from use of a cochlear implant to improve hearing of relatively high frequency sound but who have some residual hearing of relatively low frequency sound. In such a case, the recipient is forced to decide whether it will be beneficial to sacrifice any existing residual capacity to hear relatively low frequency sounds to attain the benefits of a cochlear implant to provide hearing sensation of relatively high frequency sounds.

SUMMARY

Embodiments of the present invention are generally directed to an electrode assembly comprising a low-profile, low-volume elongate electrode carrier and a corresponding guide tube for introducing the carrier into the cochlea to place electrodes disposed at the distal end of the carrier at desired locations along the tonotopically-mapped cochlea. Embodiments of the electrode assembly of the present invention facilitates intra- and extra-cochlea atraumatic implantation of the unobtrusive electrode carrier of the present invention thereby minimizing adverse impact to natural auditory functioning. For example, an electrode assembly of the present invention may be utilized to implant a carrier of the present invention into the scala tympani without damaging the delicate structures of the cochlea and without interfering with the natural hydrodynamic nature of the cochlea such as the natural flow of perilymph in the cochlea canals. In one particular embodiment, the carrier is pre-curved to attain a perimodiolar position in the scala tympani to facilitate accurate delivery of electrical stimulation with a minimum stimulation current and power consumption.

Embodiments of the electrode assembly of the present invention may be used to provide therapeutic benefits in a variety of applications. For example, the present invention may be utilized to improve the hearing of relatively high frequencies in those recipients who have residual hearing of relatively low frequencies. The spiral ganglion and other cells responsible for the perception of high frequency sounds are generally located at the basal end of the cochlea. For those individuals who suffer from high frequency hearing loss, the hair cells in the basal region of the cochlea are ineffective or otherwise damaged. In such application, cochlear implants utilizing a carrier of the present invention provide direct electrical stimulation of the basal nerve cells, thereby enhancing the hearing of high frequency sounds, while simultaneously relying on the recipient's residual hearing to sense low-to-mid-frequency sounds. This makes the electrode assembly of the present invention particularly beneficial when used in connection with stimulating auditory prostheses that are utilized as part of an electro-acoustic stimulation (EAS) device.

BRIEF DESCRIPTION OF THE DRAWINGS

Embodiments of the present invention are described below with reference to the attached drawings, in which:

FIG. 2A is a perspective, partially cut-away view of a cochlea exposing the canals and nerve fibers of the cochlea;

FIG. 4A is a schematic view of an embodiment of the electrode assembly of the present invention during implantation in a cochlea;

FIG. 4B is a schematic view of the electrode assembly illustrated in FIG. 4A shown at a time during implantation that is later in time relative to the depiction in FIG. 4A;

FIG. 4C is a schematic view of the electrode assembly illustrated in FIG. 4A shown at a time during implantation that is later in time relative to the depiction in FIG. 4B;

FIG. 4D is a schematic view of the electrode assembly illustrated in FIG. 4A shown at a time during implantation that is later in time relative to the depiction in FIG. 4C;

FIG. 4E is a schematic view of the electrode assembly illustrated in FIG. 4A shown at a time during implantation that is later in time relative to the depiction in FIG. 4D;

FIG. 7A depicts longitudinal and lateral cross-sectional views of one embodiment of a cochlear assembly in accordance with one embodiment of the present invention shown in an arrangement prior to implantation;

FIG. 7B depicts longitudinal and lateral cross-sectional views of one embodiment of a cochlear assembly in accordance with one embodiment of the present invention shown in an arrangement that occurs during implantation;

FIG. 9 is a perspective view of electrode assembly guide tube in accordance with one embodiment of the present invention;

DETAILED DESCRIPTION

Embodiments of the present invention are generally directed to an electrode assembly comprising a low-profile, low-volume elongate electrode carrier and a corresponding guide tube for introducing the carrier into the cochlea to place electrodes disposed at the distal end of the carrier at desired locations along the tonotopically-mapped cochlea. The electrode assembly of the present invention facilitates intra- and extra-cochlea atraumatic implantation of the unobtrusive electrode carrier of the present invention thereby minimizing adverse impact to natural auditory functioning. For example, as will be described in detail below, an electrode assembly of the present invention may be utilized to implant a carrier of the present invention into the scala tympani without damaging the delicate structures of the cochlea and without interfering with the natural hydrodynamic nature of the cochlea such as the natural flow of perilymph in the cochlea canals. In one particular embodiment, the carrier is pre-curved to attain a perimodiolar position in the scala tympani to facilitate accurate delivery of electrical stimulation with a minimum stimulation current and power consumption.

Embodiments of the electrode assembly of the present invention may be used to provide therapeutic benefits in a variety of applications. For example, the present invention may be utilized to improve the hearing of relatively high frequencies in those recipients who have residual hearing of relatively low frequencies. The spiral ganglion and other cells responsible for the perception of high frequency sounds are generally located at the basal end of the cochlea. For those individuals who suffer from high frequency hearing loss, the hair cells in the basal region of the cochlea are ineffective or otherwise damaged. In such application, cochlear implants utilizing a carrier of the present invention provide direct electrical stimulation of the basal nerve cells, thereby enhancing the hearing of high frequency sounds, while simultaneously relying on the recipient's residual hearing to sense low-to-mid-frequency sounds. This makes the electrode assembly of the present invention particularly beneficial when used in connection with stimulating auditory prostheses that are utilized as part of an electro-acoustic stimulation (EAS) device.

Figure 1:
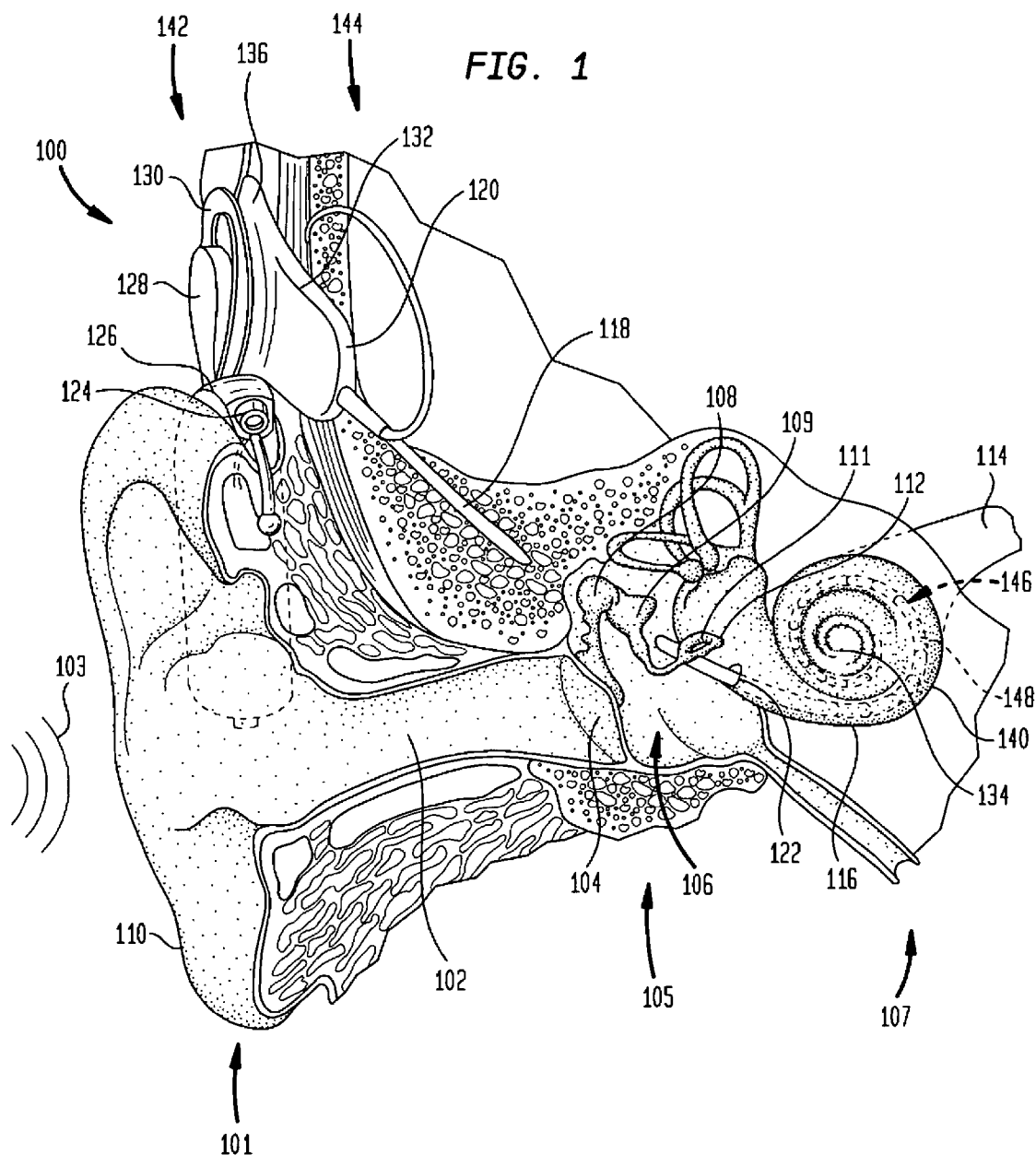
FIG. 1 is a perspective view of an implanted cochlear implant in accordance with one embodiment of the present invention.

FIG. 1 is perspective view of one embodiment of a cochlear implant 100 implanted in a human cochlea. Referring now to FIG. 1, the relevant components of outer ear 101, middle ear 105 and inner ear 107 are described next below. In a fully functional ear outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate. Such vibration sets up waves of fluid motion within cochlea 140. Such fluid motion, in turn, activates tiny hair cells (not shown) that line the inside of cochlea 140. Activation of the hair cells causes appropriate nerve impulses to be transferred through the spiral ganglion cells and auditory nerve 114 to the brain, where they are perceived as sound.

Cochlear implant 100 comprises external component assembly 142 which is directly or indirectly attached to the body of the recipient, and an internal component assembly 144 which is temporarily or permanently implanted in the recipient. External assembly 142 typically comprises microphone 124 for detecting sound, a speech processing unit 126, a power source (not shown), and an external transmitter unit 128. External transmitter unit 128 comprises an external coil 130 and, preferably, a magnet (not shown) secured directly or indirectly to external coil 130. Speech processing unit 126 processes the output of microphone 124 that is positioned, in the depicted embodiment, by auricle 110 of the recipient. Speech processing unit 126 generates coded signals, referred to herein as a stimulation data signals, which are provided to external transmitter unit 128 via a cable (not shown).

Internal assembly 144 comprises an internal receiver unit 132, a stimulator unit 120, and an elongate electrode carrier 118. Internal receiver unit 132 comprises an internal transcutaneous transfer coil 136, and preferably, a magnet (also not shown) fixed relative to the internal coil. Internal receiver unit 132 and stimulator unit 120 are hermetically sealed within a biocompatible housing. The internal coil receives power and stimulation data from external coil 130, as noted above. Elongate electrode carrier 118 has a proximal end connected to stimulator unit 120 and extends from stimulator unit 120 to cochlea 140. Electrode carrier 118 is implanted into cochlea 104 via a cochleostomy 122.

Electrode carrier 118 comprises an electrode array 146 disposed at the distal end thereof. Electrode array 146 comprises a plurality of longitudinally-aligned electrodes 148. Stimulation signals generated by stimulator unit 120 are applied by electrodes 148 to cochlear 140, thereby stimulating auditory nerve 114.

In one embodiment, external coil 130 transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 may be positioned in a recess of the temporal bone adjacent auricle 101 of the recipient.

There are several speech coding strategies that may be implemented by speech processor 126 to convert sound 103 into an electrical stimulation signal. Embodiments of the present invention may be used in combination with any speech strategy now or later developed, including but not limited to Continuation Interleaved Sampling (CIS), Spectral PEAK Extraction (SPEAK), Advanced Combination Encoders (ACE), Simultaneous Analog Stimulation (SAS), MPS, Paired Pulsatile Sampler (PPS), Quadruple Pulsatile Sampler (QPS), Hybrid Analog Pulsatile (HAPs), n-of-m and HIRES™, developed by Advanced Bionics. SPEAK is a low rate strategy that may operate within the 250-500 Hz range. ACE is a combination of CIS and SPEAK. Examples of such speech strategies are described in U.S. Pat. No. 5,271,397, the entire contents and disclosures of which is hereby incorporated by reference. The present invention may also be used with other speech coding strategies, such as low rate strategy called "Compressed Neural Coding" which is described in U.S. Pat. No. 7,822,478, issued on Oct. 26, 2010 and U.S. Pat. No. 7,272,446 issued on Sep. 18, 2007, entitled "Power Efficient Electrical Stimulation," which are hereby incorporated by reference herein.

Embodiments of cochlear implant 100 may locally store several speech strategies, such as in the form of a software program or otherwise, any one of which may be selected depending, for example, on the aural environment. For example, a recipient may choose one strategy for a low noise environment, like a conversation in an enclosed room, and second strategy for a high noise environment, like on a public street. The programmed speech strategies may be different versions of the same speech strategy, each programmed with different parameters or settings.

The successful operation of cochlear implant 100 depends in part on its ability to convey pitch information. Differing pitch percepts may be produced by cochlear implant 100 in two distinct ways. First, electrical stimulation at different sites in cochlea 140 excites different groups of neurons and because of the tonotopic arrangement of neurons in cochlea 140, different pitch sensations result. The term "tonotopic" is meant that the percept corresponding to a particular site in the cochlea changes in pitch from lower to higher as the site is changed in an apical 134 to basal 116 direction. Pitch varied in this way is known as "place pitch." Secondly different pulse rates of electrical stimulation produce different pitch sensations. Pitch varied in this way is known as "rate pitch."

Figure 2B:
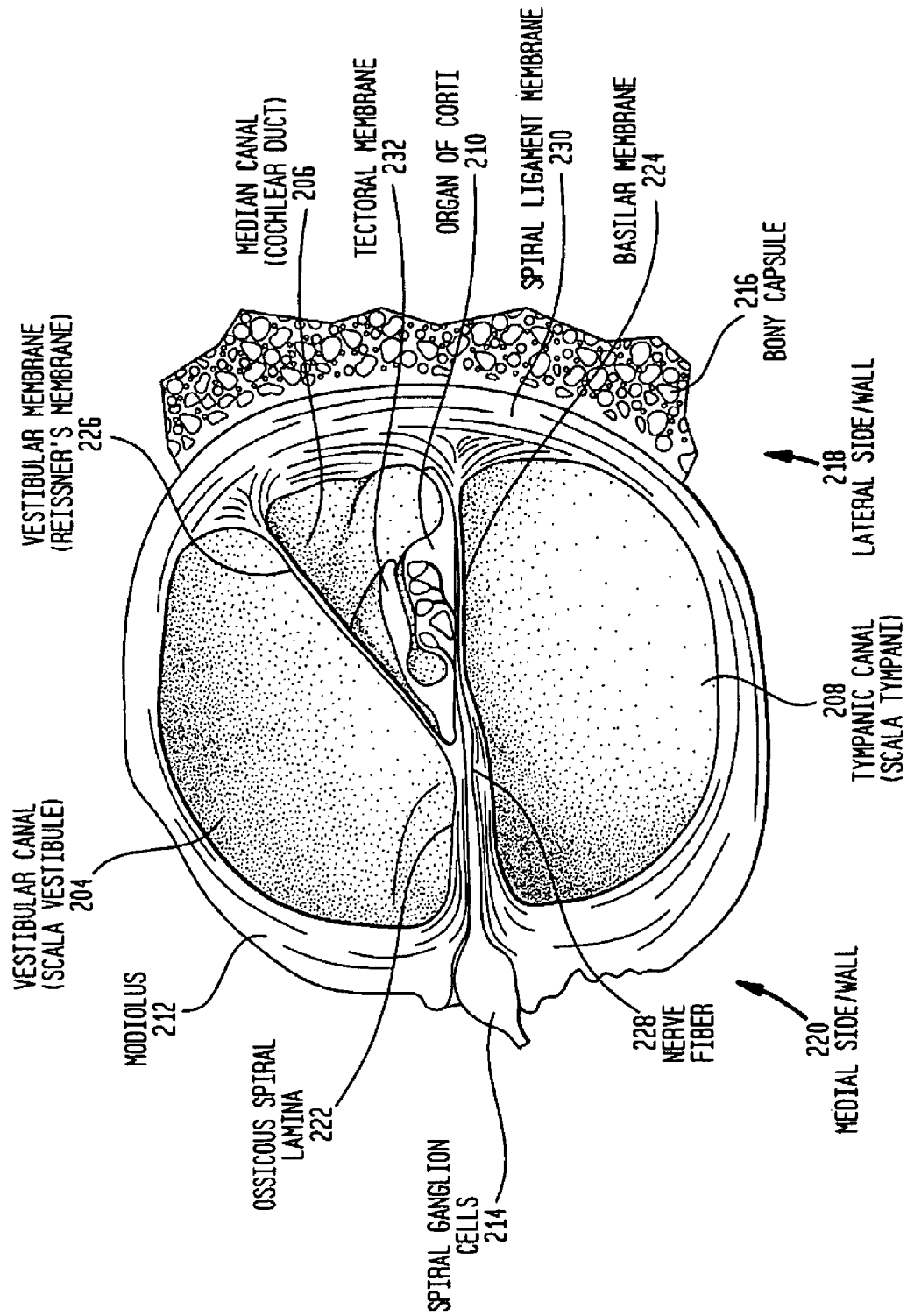
FIG. 2B is a cross-sectional view of one turn of the canals of a human cochlea.

Relevant aspects of a human cochlea is described next below with reference to FIGS. 2A and 2B. FIG. 2A is a perspective view of a human cochlea partially cut-away to display the canals and nerve fibers of the cochlea. FIG. 2B is a cross-sectional view of one turn of the canals of the cochlea illustrated in FIG. 2A. To facilitate understanding, the following description will reference the cochlea illustrated in FIGS. 2A and 2B as cochlea 140, which was introduced above with reference to FIG. 1, and which will be reference below. It should be appreciated that embodiments of the present invention may be implanted in any cochlea to provide therapeutic benefits for a variety ailments now or later discovered.

Referring to FIG. 2A, cochlea 140 is a conical spiral structure comprising three parallel fluid-filled canals, one or more of which are sometimes referred to as ducts. The canals, collectively and generally referred to herein as canals 202, comprise the tympanic canal 208, also know as the scala tympani 208, the vestibular canal 204, also referred to as the scala vestibule 204, and the median canal 206, also referred to as the cochlear duct 206. Cochlea 140 consists of a conical shaped central axis, the modiolus 212, that forms the inner wall of scala vestibule 204 and scala typani 208. Tympanic and vestibular canals 208, 204 transmit pressure, while medial canal 206 contains the organ of Corti 210 which detects pressure impulses and responds with electrical impulses which travel along the auditory nerve fibers 114 to the brain (not shown).

Referring now to FIG. 2B, separating canals 202 of cochlear 140 are various membranes and other tissue. The Ossicous spiral lamina 222 projects from modiolus 212 to separate scala vestibuli 204 from scala tympani 208. Toward lateral side 218 of scala tympani 208, a basilar membrane 224 separates scala tympani 208 from cochlear duct 206. Similarly, toward lateral side 218 of scala vestibuli 204, a vestibular membrane 226, also referred to as the Reissner's membrane 226, separates scala vestibuli 204 from cochlear duct 206.

The fluid in tympanic and vestibular canals 208, 204, referred to as perilymph, has different properties than that of the fluid which fills cochlear duct 206 and surrounds organ of Corti 210, referred to as endolymph. Sound entering auricle 110 causes pressure changes in cochlea 140 to travel through the fluid-filled tympanic and vestibular canals 208, 204. As noted, organ of Corti 210 is situated on basilar membrane 224 in cochlear duct 206. It contains rows of 16,000-20,000 hair cells (not shown) which protrude from its surface. Above them is the tectoral membrane 232 which moves in response to pressure variations in the fluid-filled tympanic and vestibular canals 208, 204. Small relative movements of the layers of membrane 232 are sufficient to cause the hair cells to send a voltage pulse or action potential down the associated nerve fiber 228. Nerve fibers 228, embedded within spiral lamina 222, connect the hair cells with the spiral ganglion cells 214 which form auditory nerve fibers 114. These impulses travel to the auditory areas of the brain for processing.

The place along basilar membrane 224 where maximum excitation of the hair cells occurs determines the perception of pitch and loudness according to the place theory. Due to this anatomical arrangement, cochlea 140 has characteristically been referred to as being "tonotopically mapped." This property of cochlea 140 has traditionally been exploited by longitudinally positioning electrodes 148 along carrier 118 to deliver to a selected region within scala tympani 208 a stimulating signal within a predetermined frequency range.

Portions of cochlear 140 are encased in a bony capsule 216. Referring to FIG. 2B, cochlear bony capsule 216 resides on lateral side 218 (the right side as drawn in FIG. 2B), of cochlea 140. Spiral ganglion cells 214 reside on the opposing medial side 220 (the left side as drawn in FIG. 2B) of cochlea 140. A spiral ligament membrane 230 is located between lateral side 218 of spiral tympani 208 and bony capsule 216, and between lateral side 218 of cochlear duct 206 and bony capsule 216. Spiral ligament 230 also typically extends around at least a portion of lateral side 218 of scala vestibuli 204.

Figure 3A:
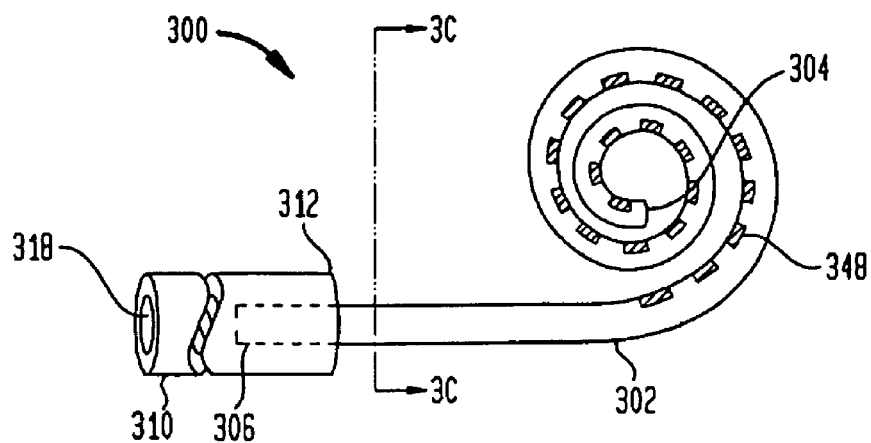
FIG. 3A is a side view of an electrode assembly in accordance with one embodiment of the present invention shown with the electrode carrier partially extending from the guide tube.
Figure 3B:
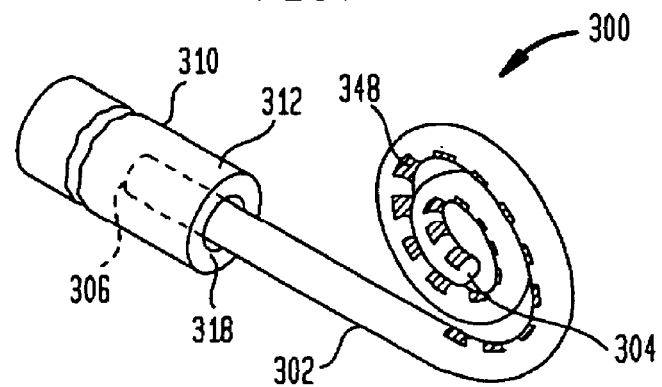
FIG. 3B is a perspective view of an electrode assembly shown in FIG. 3A.
Figure 3C:
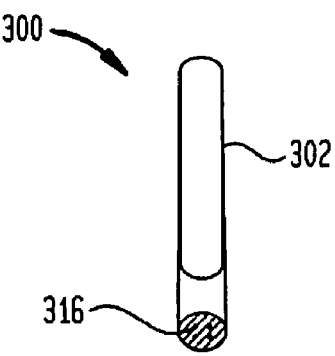
FIG. 3C is a front view of an electrode assembly shown in FIG. 3A.

FIGS. 3A and 3B are side and perspective views, respectively, of one embodiment of an electrode assembly of the present invention, referred to herein as electrode assembly 300. Electrode assembly 300 comprises an embodiment of elongate low-profile, low-volume electrode carrier 118, referred to herein as electrode carrier 302 having a distal end 304 and a proximal end 306. A guide tube 310 is shown in FIGS. 3A and 3B surrounding a proximal region of electrode carrier 302. In FIGS. 3A and 3B carrier 302 is illustrated extending from distal end 312 of guide tube 310 at which point carrier 302 takes on in a coiled configuration because this embodiment of carrier 302 is precurved in a manner disclosed elsewhere herein. It should also be appreciated that electrode carrier 302 has a plurality of electrodes 148, referred to herein as electrodes 348, disposed toward apical end 304 of carrier 302. In the embodiment shown in FIGS. 3A-3C, electrodes 348 are longitudinally-spaced to align with specific regions of tonotopically-mapped cochlea 140. FIG. 3C is a cross-sectional view of the embodiment of electrode carrier 302 taken along section line 3C-3C in FIG. 3A.

FIGS. 4A-4E are a series of side-views showing consecutive events occurring during implantation of electrode carrier 302 of electrode assembly 300. Initially, electrode carrier 302 and guide tube 310 are assembled; that is, electrode carrier 302 is slidingly inserted into lumen 318 of guide tube 310. The combined arrangement is then inserted to a predetermined depth into cochlea 140, as illustrated in FIG. 4A. Typically, such an introduction to cochlea 140 is achieved via cochleostomy 122 (FIG. 1) or through fenestra ovalis 112 (FIG. 1). In the exemplary implantation shown in FIG. 4A, the combined arrangement of carrier 302 and tube 310 is inserted to approximately the first turn of cochlea 140.

As shown in FIG. 4A, the combined arrangement of guide tube 310 and electrode carrier 302 is substantially straight. This is due in part to the rigidity of guide tube 310 relative to the force applied to the interior wall of lumen 318 (FIGS. 3A-3B) by precurved carrier 302. This prevents tube 310 from bending or curving in response to forces applied by carrier 302.

This is advantageous over conventional electrode carriers that require the use of a stylet or other positioner ("stylet" herein) to introduce the carrier to cochlea 140. As is well known to those of ordinary skill in the art, the combined conventional arrangement of a stylet and a conventional carrier member is typically curved prior to implantation. This is because such stylets are somewhat flexible. Such curvature often results in the carrier pressing up against spiral ligament membrane 230, basilar membrane 224, and other structures of cochlea 140, during implantation. This, of course, increases the likelihood that trauma occurs during implantation.

In addition, due to this flexibility of conventional electrode assemblies, there is a tendency for conventional electrode carriers to buckle during insertion, particularly when introduced via round window 112 (FIG. 1). Guide tube 310 is preferably sufficiently rigid so that it is capable of withstanding any forces normally experienced during implantation that would cause the device to bend in response to the buckling of electrode carrier 302. Furthermore, lumen 318 of guide tube 302 has an inner diameter that is just slightly greater than the outer diameter of elongate carrier 302 thereby minimizing the space between an carrier 302 and guide tube 310. This prevents elongate carrier 302 from buckling during implantation. Rather, buckling forces are transferred to rigid guide tube 310. This allows carrier 302 to remain flexible for successful implantation to a desired depth in cochlea 140. It should be appreciated that the rigidity of guide tube 310 may be determined based on other factors as well, such as the ability to bend or curve subsequent to initial implantation but desirable to have distal end 312 of guide tube 310 to reach a desired depth in, for example, cochlea 140.

In this exemplary embodiment, electrode assembly 300 is configured to place stimulating electrodes 148 as close as possible to modiolus 212 and, therefore, ganglion cells 214. To attain this, this embodiment of electrode carrier 302 is manufactured in a curved configuration; that is, precurved, as noted above. In the embodiment configured to be implanted in scala tympani 208, electrode carrier 302 is precurved to have a radius of curvature that approximates the curvature of medial side 220 of scala tympani 208. Such embodiments of the electrode assembly of the present invention are referred to as a perimodiolar electrode assembly and this position within cochlea 140 as the perimodiolar position. Advantageously, placing electrodes in the perimodiolar position provides a greater specificity of electrical stimulation, reduces the requisite current levels, and results in lower power consumption.

As shown in FIGS. 4B-4D, carrier 302 is then continually advanced through guide tube 310 while the guide tube is maintained in a substantially stationary position. This causes distal end 304 of electrode carrier 302 to extend from distal end 312 of guide tube 310. As it does so, the illustrative embodiment of carrier 302 bends or curves to attain a perimoidular position, as shown in FIGS. 4B-4D. Once carrier 302 is located at the desired depth in scala tympani 208, guide tube 310 is removed from cochlea 140 while electrode carrier 302 is maintained in a stationary position. This is illustrated in FIG. 4E.

The control of electrode carrier 302 is provided by guide tube 310, not a stylet as in conventional electrode assemblies. As such, electrode carriers of the present invention such as electrode carrier 302 do not have a lumen to receive a stylet. This is illustrated in the cross-sectional view of FIG. 3C. Further, electrode carriers of the present invention need not be manufactured with the thickness or structural integrity to ensure the electrode carrier is not punctured or torn by the stylet during implantation.

Thus, in contrast to conventional electrode carriers, electrode carriers of the present invention such as carrier 118 (FIG. 1) and 302 (FIGS. 3A-C, 4A-E) are low-profile, low-volume elongate carriers. In the embodiment illustrated in FIG. 3C, carrier 302 is substantially solid with embedded leads 316 for electrodes 148. As such, neither stylets nor positioners are factors considered when determining the physical size, shape or profile of an electrode carrier of the present invention.

In one embodiment, carrier 302 has a thickness or diameter of between approximately 0.35 and 0.55 millimeters along its length, and a diameter of approximately 0.27 millimeters at its distal end 304. In another embodiment, electrode carrier 302 has a medial length of 13.33 millimeters, which the same as the medial length of a conventional CONTOUR™ electrode carrier member available from Cochlear, Limited, Australia. A carrier 302 having the dimensions noted above has a volume of 1.769 square millimeters. This is substantially less than the volume of the noted CONTOUR™ electrode carrier, which is 8.266 square millimeters. Because the volume of such an embodiment of the electrode carrier is substantially less than convention carriers, for it is 21.4% of the volume of a conventional Contour electrode carrier (1.769/8.266=0.214), electrode carriers of the present invention is referred to as a low-profile electrode carrier. It should be appreciated that this reduction in volume is attained without reducing the quantity of electrodes disposed on the carrier.

In another embodiment, carrier 302 has a thickness or diameter of between approximately 0.25 and 0.65 millimeters along its length, and a diameter of between approximately 0.25 and 0.35 millimeters at its distal end 304. As one of ordinary skill in the art would appreciate, such dimensions are exemplary only, and electrode carriers of the present invention may be provided with other dimensions due to the elimination of a stylet lumen.

The above reduction in carrier volume may be achieved, for example, by reducing the cross-sectional area of the carrier by approximately 50%, either uniformly or non-uniformly, using existing manufacturing technology. As one of ordinary skill in the art would appreciate, the thickness or diameter of electrode carrier 302 is dependent on the selected materials and manufacturing processes, and that carriers much thinner than those noted above may be manufactured, and are considered to be within the scope of the present invention.

It should be appreciated that, as noted, lumen 318 of embodiments of guide tube 310 has a diameter that is suitable to slidingly receive the embodiment of low-profile, low-volume elongate carrier 302 that is implemented in electrode assembly 300. Guide tube 310, as noted, is further configured to introduce carrier 302 into cochlea 140 so as to place electrodes 348 disposed at distal end 304 of carrier 302 at desired locations along tonotopically mapped cochlea 140. Preferably, guide tube 310 is sufficiently thin to achieve this while facilitating intra- and extra-cochlea atraumatic implantation of carrier 302.

In the embodiments illustrated in FIGS. 3A and 3B, the cross-sectional profile of guide tube 310 is round. It should be appreciated, however, that embodiments of the guide tube of the present invention may have any cross-sectional profile suitable for a particular application. For example, in alternative embodiments, the guide tube has an oval or rectangular cross-sectional profile.

Also, embodiments of the guide tube of the present invention may be constructed from ay suitable material or combination of materials now or later developed that are appropriate or acceptable for a given application. Such materials may include, but are not limited, to, polymers, metals, combination of fixed and bioresorbable polymers, etc. In one embodiment, the guide tube is constructed from one or more bioresorbable materials so that once the electrode carrier is implanted and the guide tube is retracted, the guide tube may remain surrounding the extra-cochlear carrier 302 to be resorbed over a specified period of time. In one embodiment, the bioresorbable guide tube remains within the mastoid cavity to be entirely resorbed extra-cochlearly. As one of ordinary skill in the art would appreciate, the bioresorbable material would be selected to have a specified rate of resorption such that the guide tube would be completely resorbed after, for example, 2-4 weeks; that is, prior to when cochlear implant 100 is initially powered on. As is also apparent to those of ordinary skill in the art, there are many bioresorbable materials available with a few having proven biocompatibility and FDA approval. Examples include but are not limited to those based on PLA (polylactic acid) or PGA (polyglycolic acid).

In one embodiment, the guide tube is constructed from a bioresorbable material that is impregnated or coated with a compound or combination of compounds suitable for achieving one or more desired functions. For example, in some embodiments, an anti-bacterial or anti-inflammatory (or other) compound is impregnated in or coated on the guide tube to, for example, prevent infection, reduce fluid accumulation, tissue inflammation, etc.

In alternative embodiments, the guide tube is coated or impregnated to provide one or more other properties in addition to or in the alternative to those identified above. For example, in one embodiment, the guide tube is coated or impregnated with a compound that contributes to the lubricity of the associated electrode carrier. In another embodiment, the guide tube is coated or impregnated with a compound that contributes to drug elution of the implanted elongate low-profile, low-volume electrode carrier.

Figure 5:
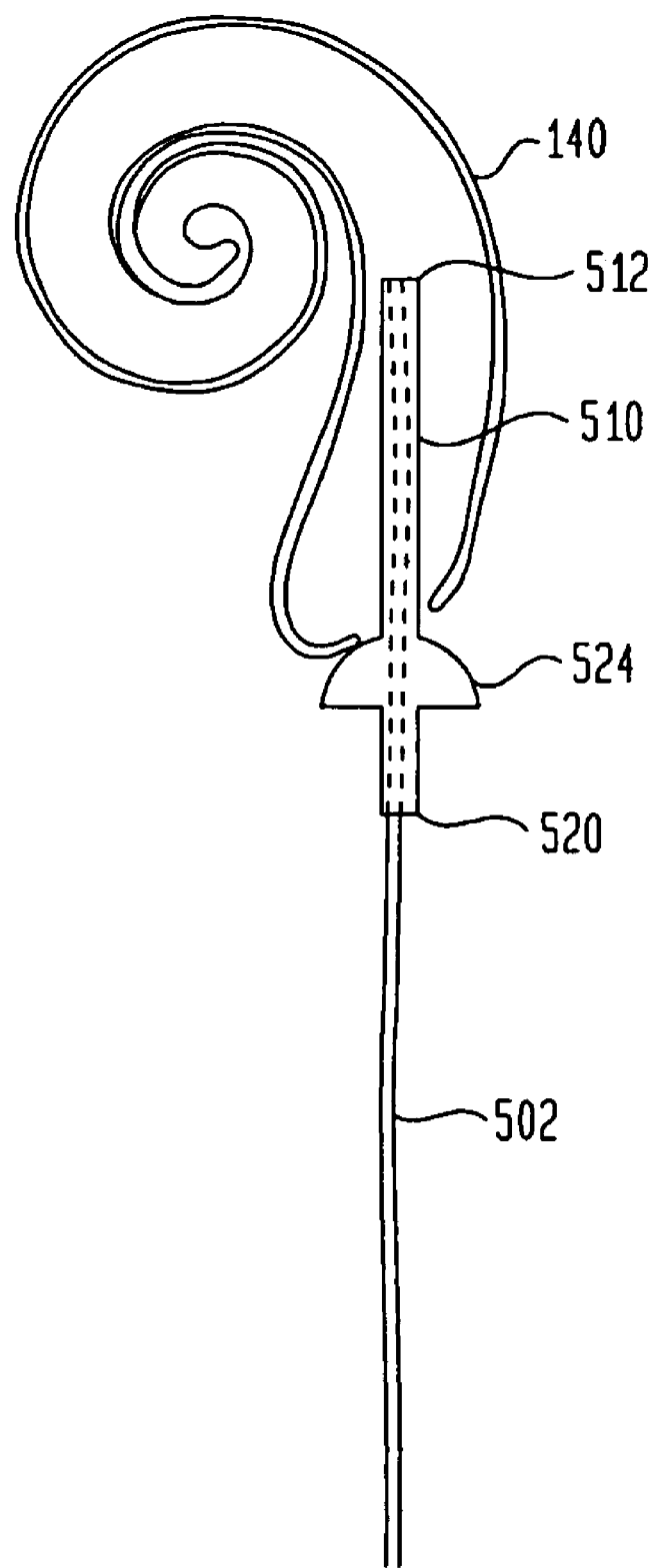
FIG. 5 is a schematic side view of one embodiment of an electrode assembly of the present invention that facilitates placement of the electrode carrier at a desired depth in the cochlea.

FIG. 5 is a schematic side view of one embodiment of an electrode assembly of the present invention that facilitates placement of an electrode carrier at a desired depth in cochlea 140. The embodiment of the electrode assembly of the present invention illustrated in FIG. 5 is referred to herein as electrode assembly 500. Electrode assembly 500 comprises an embodiment of guide tube 310 (FIGS. 3A and 3B), referred to herein as guide tube 510, and an embodiment of elongate low-profile, low-volume electrode carrier 118, referred to herein as carrier 502. In the arrangement illustrated in FIG. 5, electrode carrier 502 is located within guide tube 510, and the combined arrangement has be implanted in cochlea 140 up to the first turn of the cochlea.

Proximal end 520 of guide tube 510 comprises a radially-extending extension 524 that serves as means to assist the audiologist in determining the appropriate depth at which to implant guide tube 502. For example, in the embodiment shown in FIG. 5, guide tube 502 is configured to abut cochlea 140 when distal end 512 of guide tube 510 is located at the first turn of cochlea 140. In alternative embodiments extension 524 may provide an indication of an insertion depth rather than cease advancement of electrode assembly 500.

As one of ordinary skill in the art would appreciate, extension 524 may have different configurations in alternative embodiments of the present invention. For example, in one alternative embodiment, extension 524 is formed as an extension arm that extends from a relatively small radius on guide tube 510.

In one embodiment, extension 524 is further configured to provide a surface that may be used by the audiologist to grip and position guide tube 510 and carrier 502 during implantation.

It should also be appreciated that a stopper may be implemented to provide visual rather than physical feedback to the implanting audiologist. For example, in one embodiment, a stopper is implemented as a marker located on the surface of the guide tube that is visible to the implanting audiologist until the guide tube is inserted into cochlea 140 beyond a desired depth. At that point the visible marker is no longer visible, indicating to the audiologist that the guide tube is at the desired depth. Alternative embodiments may include multiple markers each indicating a different insertion depth has been achieved. It should be appreciated that an extension, marker and/or other similar elements may be incorporated in any combination in alternative embodiments of the present invention.

Figure 6A:
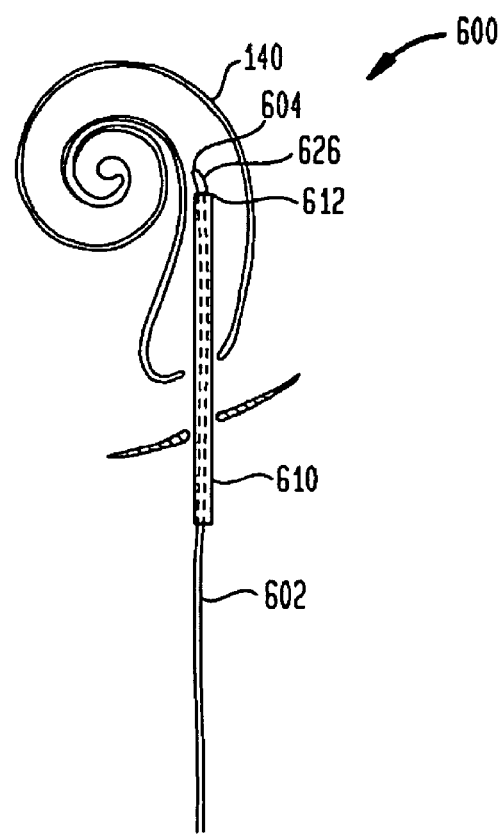
FIG. 6A is a schematic side view of an elongate electrode carrier assembly having a tip in accordance with one embodiment of the present invention shown during implantation.
Figure 6B:
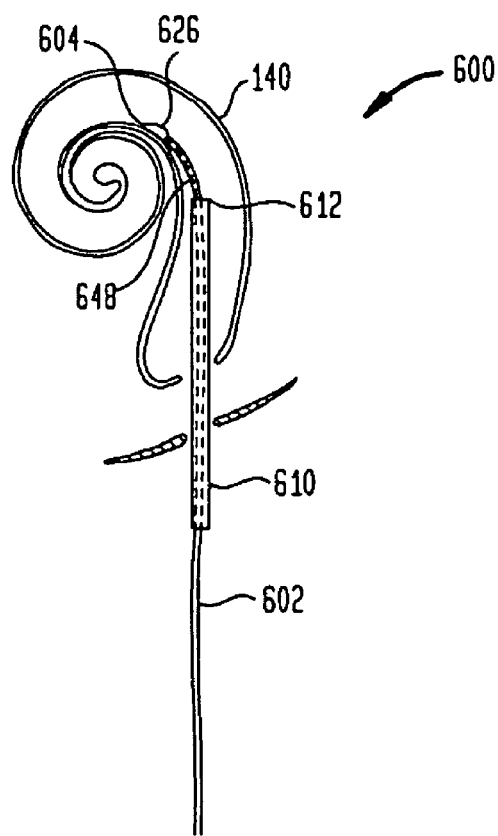
FIG. 6B is a schematic side view of an elongate electrode carrier assembly of FIG. 6A shown at some later point during implantation.

FIG. 6A is a schematic side view of an elongate electrode carrier assembly in accordance with one embodiment of the present invention shown during implantation. FIG. 6B is a schematic side view of an elongate electrode carrier assembly of FIG. 6A shown at some later point during implantation. The electrode assembly shown in FIGS. 6A and 6B, referred to herein as electrode assembly 600, comprises a low-profile, low-volume elongate electrode carrier 602 and an associated guide tube 610, constructed and arranged in accordance with the teachings of the present invention. In this embodiment, distal end 612 of guide tube 610 interacts with distal end 604 of electrode carrier 602 to prevent the sheath from sliding off the carrier; that is, to maintain a relative longitudinal position. In this embodiment, a barb or hooked tip 626 is disposed at distal end 602 of carrier 602 prevents the carrier from being accidentally withdrawn from the guide tube during surgery or handling. Barb 626 may also be used to orientate electrode carrier 602. In one embodiment, barb 626 is in the form of a soft silicone extension disposed at distal end 604.

FIG. 7A depicts longitudinal and lateral cross-sectional views of one embodiment of a cochlear assembly in accordance with one embodiment of the present invention shown in an arrangement prior to implantation. FIG. 7B depicts longitudinal and lateral cross-sectional views of the embodiment of the cochlear assembly illustrated in FIG. 7A shown in an arrangement that occurs during implantation. In this embodiment, electrode assembly 700 comprises an embodiment of guide tube 310, referred to herein as guide tube 710, and an embodiment of carriers 118 and 302, referred to herein as electrode carrier 702.

Electrode carrier 702 is, in this embodiment, tapered. Guide tube 710 is made of a flexible material so that it may be tapered to hug the profile of tapered electrode carrier 702, as shown in FIGS. 7A and 7B. The taper could be achieved by having a flexible guide tube that expanded as electrode carrier 702 is slidingly advanced through tube 710.

In the embodiment illustrated in FIGS. 7A and 7B, guide tube 710 has an axial slit 703 to guide electrode carrier 702 which, in this embodiment, has a corresponding mating feature 705. In alternative embodiments, axial slit 703 is further configured to be used to split guide tube 710 for removal, or to allow guide tube 710 to be adapted to an external tool for automated insertion.

Figure 7C:
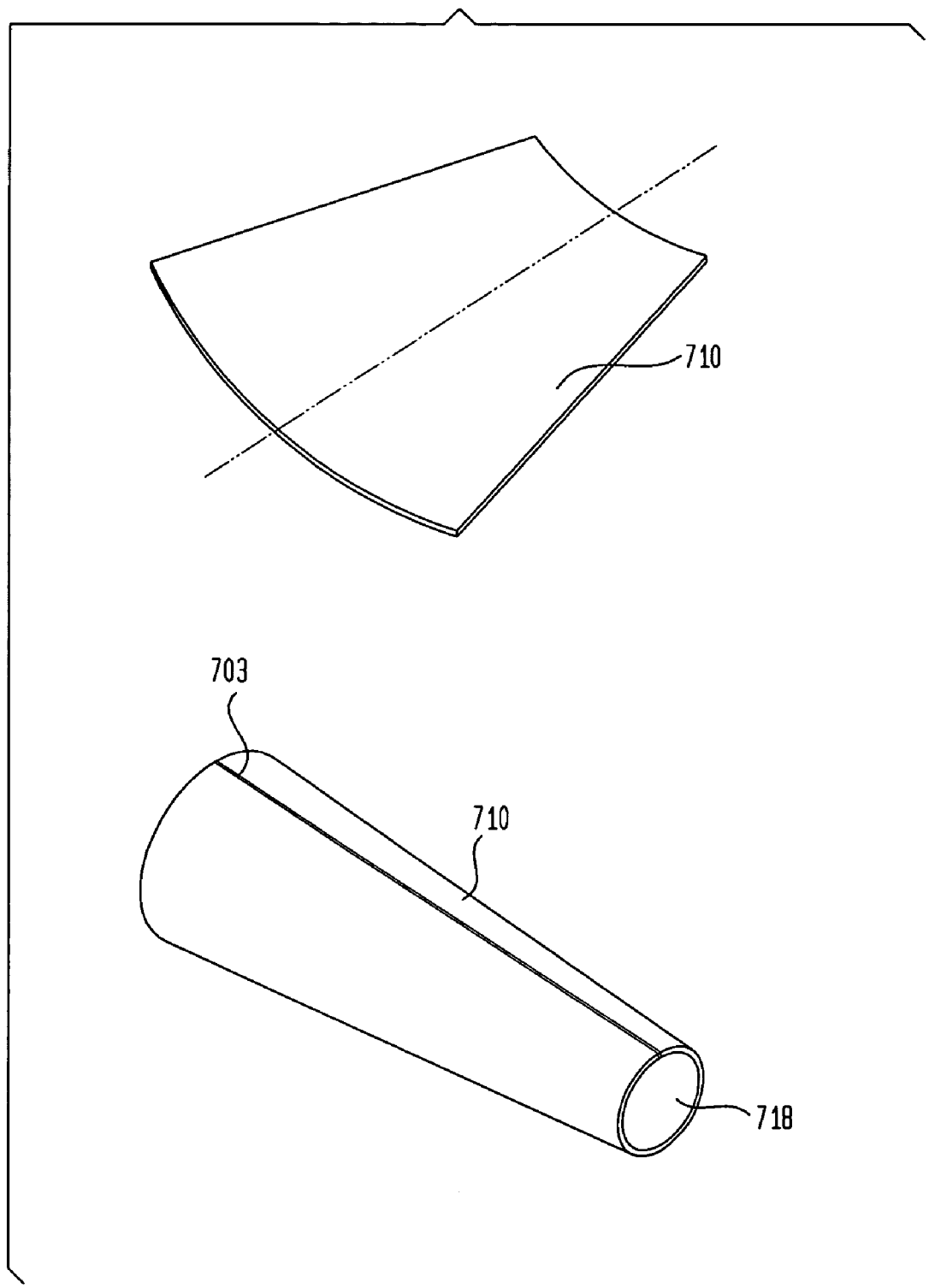
FIG. 7C is a perspective view of a tapered guide tube shown in a flat and rolled configuration, in accordance with one embodiment of the present invention.

Referring to FIG. 7C, to achieve a tapered guide tube 710 that is also removable, a rolled design may be applied in which a thin flat sheet of material is rolled to a specified tapered profile that will keep electrode carrier 702 straight for insertion, but can also then expand as the carrier is advanced. Once guide tube 710 is withdrawn, it can then be unrolled from the lead connecting carrier 702 to stimulator unit 120 (FIG. 1) and disposed.

Figure 8A:
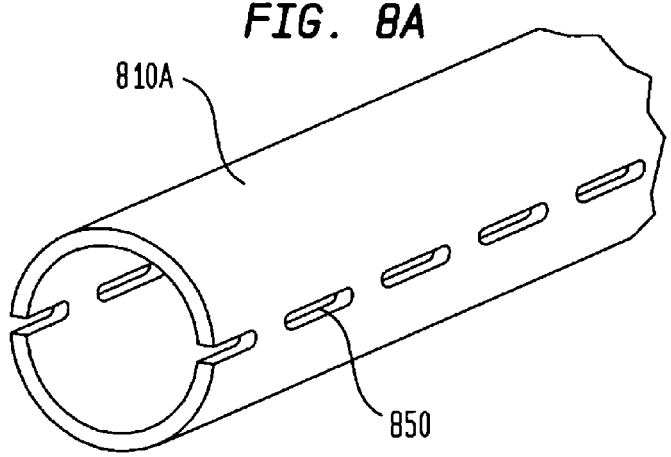
FIG. 8A is a perspective view of electrode assembly guide tube in accordance with one embodiment of the present invention.
Figure 8B:
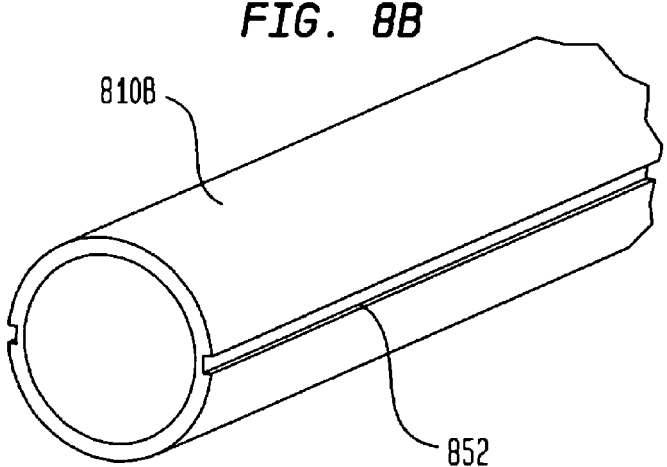
FIG. 8B is a perspective view of electrode assembly guide tube in accordance with one embodiment of the present invention.
Figure 8C:
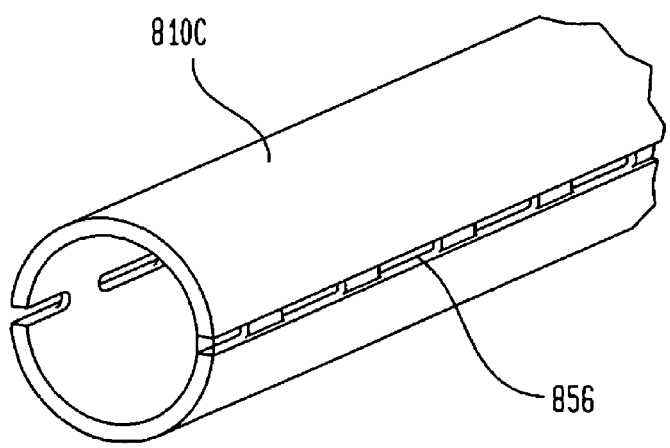
FIG. 8C is a perspective view of electrode assembly guide tube in accordance with one embodiment of the present invention.

FIGS. 8A-8C are perspective views of alternative embodiments of the guide tube of the present invention, referred to herein as guide tubes 810A, 810B and 810C, respectively. Guide tubes 810 incorporate through channels 850 as shown in guide tube 810A in FIG. 8A, recessed 852 as shown in guide tube 810B in FIG. 8B, serrations 856 as shown in guide tube 810C in FIG. 8C, or any other feature or combination of features that form a weak point that allows the guide tube to be split or peeled apart after withdrawal of the guide tube from around the electrode carrier or the lead connecting the electrode carrier to stimulator unit 120 (FIG. 1). These could be single or multiple features allowing the guide tube to be split into one or more separate pieces to facilitate removal of the guide tube after implantation.

FIG. 9 is a perspective view of electrode assembly guide tube in accordance with one embodiment of the present invention. This embodiment of the guide tube, referred to herein as guide tube 910, is configured to be flexible only in a selected direction. There are two longitudinal planes extending through guide tube 902. On opposing sides of guide tube 902 there are longitudinally-spaced slots each of which is approximately centered on longitudinal plane 960. As a result, guide tube 902 is flexible about plane 962, referred to as flexible plane 962, and is not flexible about longitudinal plane 960, referred to as rigid plane 960.

This embodiment of the guide tube enables the audiologist to better control the electrode assembly. For example, guide tube 910 enables an audiologist to hold the electrode carrier (not shown) straight, and after insertion of the electrode carrier, guide tube 902 is withdrawn, remaining around the carrier or lead wires. At that point, guide tube 902 may be rotated and bent around flexible plane 902. As such, guide tube 902 also serves as a protective sheath around the lead, protecting it from external impact etc.

Figure 10A:
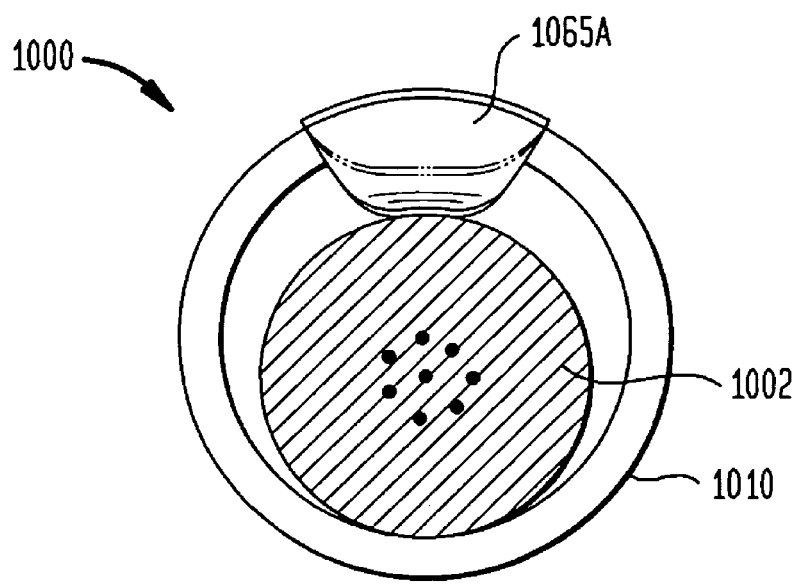
FIG. 10A is a perspective view of an alternative embodiment of a guide tube of the present invention.
Figure 10B:
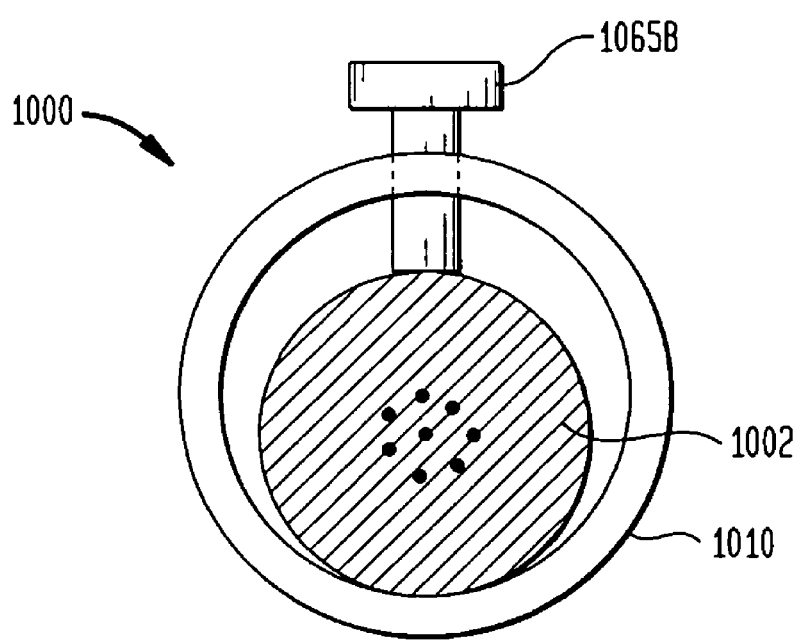
FIG. 10B is a perspective view of an alternative embodiment of a guide tube of the present invention.

In the embodiment shown in FIGS. 10A and 10B, an embodiment of guide tube 310, referred to herein as guide tube 1000, is configured to incorporate a "brake" 1065 that holds an embodiment of electrode carrier 118, referred to herein as electrode carrier 1002, in place within the guide tube to prevent the carrier from displacing or rotating within the guide tube during transportation and handling. Once guide tube 1010 and electrode carrier 1002 are implanted, brake 1065 may be removed or adjusted so that the carrier may be advanced and the guide tube withdrawn. This ensures electrode carrier 1002 is in the correct position and orientation upon insertion.

In the embodiment illustrated in FIG. 10A, brake 1065A is implemented as a simple silicone flap on proximal end 1020 of guide tube 1010 that mates with and applies pressure to electrode carrier 1002 when the carrier is disposed in lumen 1018 of the guide tube so as to prevent relative displacement. Once guide tube 1010 is properly positioned in cochlea 140, flap 1065A may be lifted thereby allowing electrode carrier 1002 to be slidingly advanced through guide tube 1010.

In the embodiment illustrated in FIG. 10B, a brake 1065B is implemented as a separate peg that clamps electrode carrier 1002 to guide tube 1010. Once the electrode assembly 1000 is in position in cochlea 140, peg 1065B can be removed thereby allowing electrode carrier 1002 to be slidingly advanced through guide tube 1010.

As one of ordinary skill in the art would appreciate, other implementations of brake 665 may be utilized depending on the particular application.

Figure 11A:
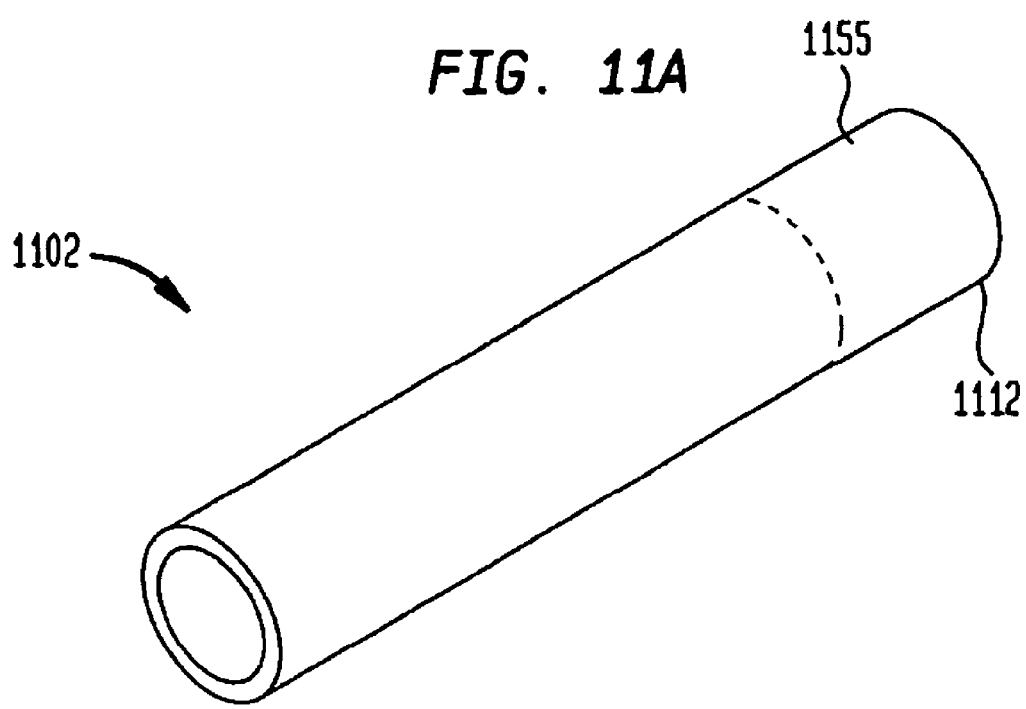
FIG. 11A is a perspective view of an alternative embodiment of a guide tube of the present invention.
Figure 11B:
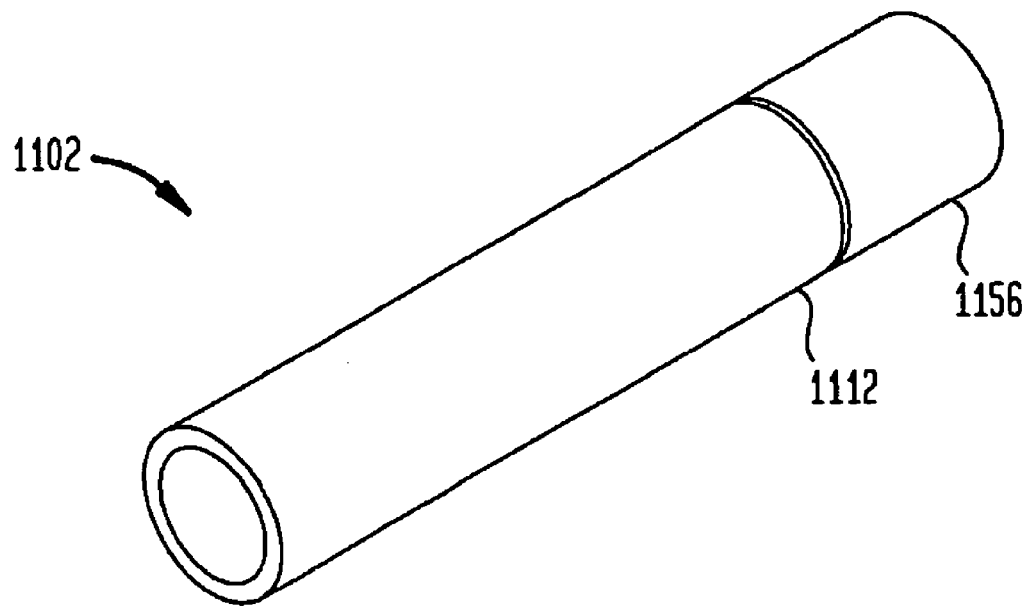
FIG. 11B is a perspective view of an alternative embodiment of a guide tube of the present invention.

FIG. 11A is a perspective view of an embodiment of the guide tube of the present invention having a function tip, referred to herein as guide tube 1102. Referring to FIG. 11A, guide tube 1102 has a unitary or integrated distal end 1112 defining a tip 1155 suitable for performing one or more functions. For example, in one embodiment, guide tube 1102 incorporates a tip 1155 that is more malleable, or softer than the rest of the guide tube to reduce potential damage to cochlea 140. This may be achieved by modifying the material properties of distal end 1112 or by adding an addition section 1156 of soft material such as silicone, Eurathane, PEBAX, etc., as shown in FIG. 11B In one embodiment, the material properties of distal end 1112 of guide tube 1102 may be modified such that, for a bioresorbable material, a section 1155 of the distal end may contain less molecular binder such that tip 1155 is softer/more flexible, but also to not dissolve while still in cochlea 140.

In another embodiment, a length of guide tube 1102 may be constructed from different layers; that is, a laminate, of polymer materials of differing stiffness. For example, a section of distal end 1112 may then have specific layer(s) removed using a chemical or laser etching process, leaving only flexible layers for tip 1155 and a more rigid proximal region. Alternatively, a polymer or silicone material having a high temperature cure may be used such that localized heating may be applied during the curing process such that the tip is not fully cured and hence softer/more flexible.

The dimensions of an attached soft tip would be of equivalent inner diameter and outer diameter to the guide tube itself. The length would be such that its rigidity is sufficient to maintain an associated electrode carrier in a straight configuration, yet long enough to safely deflect/flex when inserted to cochlea 140. In one embodiment, this length is between 2 and 4 mm.

Figure 12:
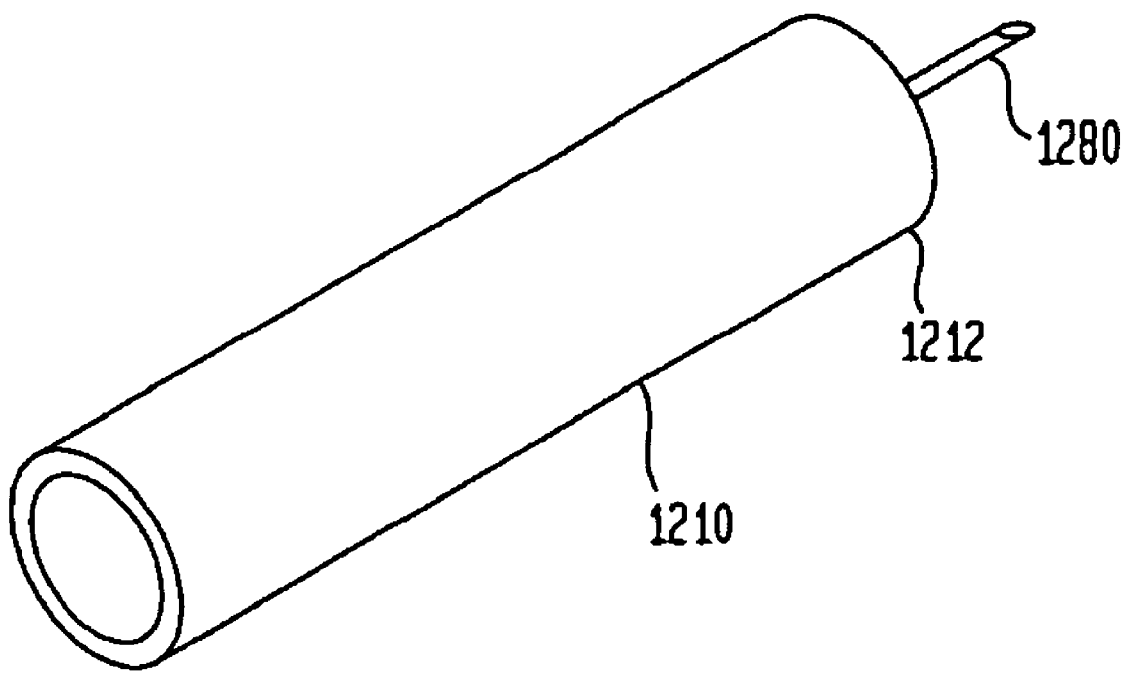
FIG. 12 is a perspective view of an alternative embodiment of a guide tube of the present invention.

FIG. 12 is a perspective view of an alternative embodiment of a guide tube of the present invention, referred to herein as guide tube 1210. In this embodiment, a surgical tool 1280 is secured to a distal end 1212 of guide tube 1210 to incise the round window membrane or endosteum immediately prior to insertion reducing the risk of leaking perilymph. In such an embodiment, surgical tube 1280 is a rigid, sharp cutting surface similar to that found at the end of a syringe needle. This enables such a tip to perforate the round window membrane during insertion (in the one action). Guide tube 1210 may then continue to be inserted utilizing, for example, image guided surgery, so that the tip does not contact other structures of cochlea 140.

Advantageously, perforation of the round window (or exposed endosteum for a cochleostomy insertion) in this manner eliminates the delay traditionally experienced between perforation and insertion of the electrode carrier. Immediate insertion after perforation prevents perilymph from escaping, and prevents blood, bone dust or other foreign matter from entering the cochlea. Any one of such occurrences may be detrimental to preservation of residual hearing.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An electrode assembly for implanting electrodes in a cochlea of a recipient, comprising:
    a flexible, elongate electrode carrier configured to have a spiral configuration such that bias forces are exerted by said electrode carrier when arranged in a non-spiral position; and
    an elongate guide tube having interior dimensions defining a lumen for slidingly retaining the carrier, and exterior dimensions that enable the guide tube to be inserted into the recipient's cochlea, the guide tube comprising a rigid tube body and a distal end region sufficiently flexible to bend in response to said bias forces applied to the distal end region by the electrode carrier when the electrode carrier is positioned within the lumen, such that the distal end region curves to cause the electrode carrier to follow a trajectory not parallel with a longitudinal axis of the rigid tube body as the carrier exits the guide tube.

2. The electrode assembly of claim 1, wherein a first longitudinal imaginary plane extends through the guide tube and a second longitudinal imaginary plane extends through the guide tube and substantially orthogonal to the first plane, wherein the guide tube further comprises:
    one or more longitudinally-spaced slots substantially aligned along the first plane and disposed along a side of the elongate tube, wherein the longitudinally-space slots are configured to allow the guide tube to bend in a direction within the first plane.

3. The electrode assembly of claim 1, wherein the distal end region is formed separately from the rigid tube body and subsequently fixed to the distal end of the rigid tube body.

4. The electrode assembly of claim 1, wherein the guide tube comprises two or more layers, and further wherein the distal end region is formed by removing one or more layers from the guide tube.

5. The electrode assembly of claim 4, wherein the one or more layers of the guide tube are configured to be removable by chemical removal.

6. The electrode assembly of claim 4, wherein the one or more layers of the guide tube are configured to be removable by laser removal.

7. The electrode assembly of claim 1, wherein the distal end region is configured as a fraction of a tube.

8. The electrode assembly of claim 1, wherein the surface of the distal end region is configured as a corrugated or convoluted surface.

9. The electrode assembly of claim 1, wherein the surface of the distal end region comprises one or more slits configured to allow the distal end region to bend.

10. The electrode assembly of claim 1, wherein the rigid guide tube comprises a braid structure configured to provide rigidity to the rigid guide tube.

11. The electrode assembly of claim 1, wherein the carrier is pre-curved to attain a perimodiolar position in the scala tympani of the cochlea when implanted.

12. The electrode assembly of claim 1, wherein the guide tube and carrier are configured to implant the carrier into the scala tympani without substantial damage to the cochlea.

13. The electrode assembly of claim 1, wherein the carrier is configured to be implanted into the scala tympani, and to minimally interfere with the natural hydrodynamic nature of the cochlea.

14. The electrode assembly of claim 1, wherein the carrier has an outer diameter and wherein the guide tube has an inner diameter that is minimally greater than the outer diameter of the carrier.

15. The electrode assembly of claim 1, wherein the carrier has a diameter of between approximately 0.35 and 0.55 millimeters along its length, and a diameter of approximately 0.27 millimeters at its distal end.

16. The electrode assembly of claim 1, wherein the carrier has a diameter of between approximately 0.35 and 0.55 millimeters along its length.

17. The electrode assembly of claim 16, wherein the carrier has a diameter of approximately 0.27 millimeters at its distal end.

18. The electrode assembly of claim 1, wherein the carrier has a medial length of approximately 13.33 millimeters.

19. The electrode assembly of claim 1, wherein the carrier has a volume of approximately 1.8 square millimeters.

20. The electrode assembly of claim 1, wherein the carrier has a diameter of between approximately 0.25 and 0.65 millimeters along its length.

21. The electrode assembly of claim 1, wherein the carrier has a diameter of between approximately 0.25 and 0.35 millimeters at its distal end.

22. The electrode assembly of claim 1, wherein the guide tube is constructed from one or more bioresorbable materials.

23. The electrode assembly of claim 22, wherein the bioresorbable materials is a compound selected from a group consisting of anti-bacterial, anti-inflammatory, and antibiotic.

24. The electrode assembly of claim 22, wherein the bioresorbable materials has a drug elution enhancing compound disposed therein.

25. The electrode assembly of claim 1, wherein the guide tube further comprises a radially-extending extension configured to indicate when the guide tube has been inserted to a predetermined depth into the cochlea.

26. The electrode assembly of claim 1, wherein the distance between the radially-extending extension and the distal end of the guide tube is approximately 6.5 mm.

27. The electrode assembly of claim 26, wherein the radially-extending extension is configured to abut the cochlea during insertion of the guide tube into the cochlea.

28. The electrode assembly of claim 27, wherein the radially-extending extension is configured to abut the cochlea when the distal end of the guide tube is inserted to the first turn of the cochlea.

29. The electrode assembly of claim 28, wherein the distal end of the guide tube and the distal end of the carrier are configured to interact to maintain a relative longitudinal position of the carrier and guide tube.

30. The electrode assembly of claim 1, wherein the carrier is tapered along a substantially substantial portion of its length and the guide tube is formed from a flexible material and has an interior diameter that is less than an exterior diameter of the carrier at a point adjacent to the distal end, wherein the guide tube expands to hug the tapered electrode carrier.

31. The electrode assembly of claim 1, wherein the guide tube has one or more regions of weakness configured to enable portions of the guide tube to be removed.

32. The electrode assembly of claim 31, wherein the one or more regions of weakness are formed by disposing one or more channels longitudinally along the guide tube.

33. The electrode assembly of claim 31, wherein the one or more regions of weakness are formed by disposing one or more recesses longitudinally along the guide tube.

34. The electrode assembly of claim 31, wherein the one or more regions of weakness are formed by disposing one or more serrations longitudinally along the guide tube.

35. The electrode assembly of claim 1, wherein the guide tube further comprises a releasable brake constructed and arranged to hold the carrier in place within the guide tube to prevent the carrier from displacing or rotating within the guide tube.

36. The electrode assembly of claim 35, wherein the brake comprises one or more flaps extending into the lumen of the guide tube, configured to apply pressure on the carrier.

37. The electrode assembly of claim 35, wherein the brake comprises one or more protuberances extending into the lumen of the guide tube, configured to apply pressure on the carrier.

38. The electrode assembly of claim 35, wherein the brake is configured to be at least partially removable from the guide tube.

39. The electrode assembly of claim 1, wherein the guide tube further comprises a surgical tool secured to the distal end of the guide tube.

40. The electrode assembly of claim 1, wherein the distal end region has a length of approximately 2-4 mm.

41. An electrode assembly for implantation in a cochlea of a recipient, comprising:
   a flexible, elongate electrode carrier configured to have a spiral configuration such that bias forces are exerted by said electrode carrier when arranged in a non-spiral position; and
   an elongate guide tube comprising a rigid tube body, having interior dimensions defining a lumen for slidingly retaining the carrier, and exterior dimensions configured to allow said guide tube to be inserted through a cochleostomy region in the recipient's cochlea; and
   wherein the guide tube has one or more regions of weakness configured to enable portions of the guide tube to be removed.

42. The electrode assembly of claim 41, wherein a distal end region is configured as a fraction of a tube.

43. The electrode assembly of claim 41, wherein the surface of a distal end region is configured as a corrugated or convoluted surface.

44. The electrode assembly of claim 41, wherein the rigid guide tube comprises a braid structure configured to provide rigidity to the rigid guide tube.

45. The electrode assembly of claim 41, wherein the carrier is pre-curved to attain a perimodiolar position in the scala tympani of the cochlea when implanted.

46. The electrode assembly of claim 41, wherein the guide tube and carrier are configured to implant the carrier into the scala tympani without substantial damage to the cochlea.

47. The electrode assembly of claim 41, wherein the carrier is configured to be implanted into the scala tympani, and to minimally interfere with the natural hydrodynamic nature of the cochlea.

48. The electrode assembly of claim 41, wherein the carrier has an outer diameter and wherein the guide tube has an inner diameter that is minimally greater than the outer diameter of the carrier.

49. The electrode assembly of claim 41, wherein the carrier has a diameter of between approximately 0.35 and 0.55 millimeters along its length, and a diameter of approximately 0.27 millimeters at its distal end.

50. The electrode assembly of claim 41, wherein the carrier has a diameter of between approximately 0.35 and 0.55 millimeters along its length.

51. The electrode assembly of claim 50, wherein the carrier has a diameter of approximately 0.27 millimeters at its distal end.

52. The electrode assembly of claim 41, wherein the carrier has a medial length of approximately 13.33 millimeters.

53. The electrode assembly of claim 41, wherein the carrier has a volume of approximately 1.8 square millimeters.

54. The electrode assembly of claim 41, wherein the carrier has a diameter of between approximately 0.25 and 0.65 millimeters along its length.

55. The electrode assembly of claim 41, wherein the carrier has a diameter of between approximately 0.25 and 0.35 millimeters at its distal end.

56. The electrode assembly of claim 41, wherein the guide tube is constructed from one or more bioresorbable materials.

57. The electrode assembly of claim 56, wherein the bioresorbable materials is a compound selected from a group consisting of anti-bacterial, anti-inflammatory, and antibiotic.

58. The electrode assembly of claim 56, wherein the bioresorbable materials has a drug elution enhancing compound disposed therein.

59. The electrode assembly of claim 41, wherein the guide tube further comprises a radially-extending extension configured to indicate when the guide tube has been inserted to a predetermined depth into the cochlea.

60. The electrode assembly of claim 41, wherein the distance between the radially-extending extension and a distal end of the guide tube is approximately 6.5 mm.

61. The electrode assembly of claim 60, wherein the radially-extending extension is configured to abut the cochlea during insertion of the guide tube into the cochlea.

62. The electrode assembly of claim 61, wherein the radially-extending extension is configured to abut the cochlea when a distal end of the guide tube is inserted to the first turn of the cochlea.

63. The electrode assembly of claim 62, wherein a distal end of the guide tube and the a end of the carrier are configured to interact to maintain a relative longitudinal position of the carrier and guide tube.

64. The electrode assembly of claim 41, wherein the one or more regions of weakness are formed by disposing one or more channels longitudinally along the guide tube.

65. The electrode assembly of claim 41, wherein the one or more regions of weakness are formed by disposing one or more recesses longitudinally along the guide tube.

66. The electrode assembly of claim 41, wherein the one or more regions of weakness are formed by disposing one or more serrations longitudinally along the guide tube.

67. The electrode assembly of claim 41, wherein the guide tube further comprises a releasable brake constructed and arranged to hold the carrier in place within the guide tube to prevent the carrier from displacing or rotating within the guide tube.

68. The electrode assembly of claim 67, wherein the brake comprises one or more flaps extending into the lumen of the guide tube, configured to apply pressure on the carrier.

69. The electrode assembly of claim 66, wherein the brake comprises one or more protuberances extending into the lumen of the guide tube, configured to apply pressure on the carrier.

70. The electrode assembly of claim 66, wherein the brake is configured to be at least partially removable from the guide tube.

71. The electrode assembly of claim 41, wherein the guide tube further comprises a surgical tool secured to a distal end of the guide tube.

72. The electrode assembly of claim 65,
wherein the a flexible, elongate electrode carrier comprises a plurality of electrodes longitudinally disposed along the carrier; and
wherein the longitudinally disposed regions of weakness are located on the guide tube such that when the guide tube slidingly retains the carrier, the regions of weakness are spaced away from the electrodes.

* * * * *